(12) United States Patent
Pompejus et al.

(10) Patent No.: US 6,927,026 B1
(45) Date of Patent: Aug. 9, 2005

(54) OROTIDINE-5'-PHOSPHATE DECARBOXYLASE-GENE, GENE CONSTRUCT CONTAINING SAID GENE AND THE UTILIZATION THEREOF

(75) Inventors: Markus Pompejus, Waldsee (DE); Jose Luis Revuelta Doval, Salamanca (ES); Maria Angeles Santos Garcia, Salamanco (ES)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/582,779
(22) PCT Filed: Dec. 18, 1998
(86) PCT No.: PCT/EP98/08382
§ 371 (c)(1),
(2), (4) Date: Jul. 3, 2000
(87) PCT Pub. No.: WO99/36432
PCT Pub. Date: Jul. 22, 1999

(30) Foreign Application Priority Data

Jan. 15, 1998 (DE) .......................................... 198 01 120

(51) Int. Cl.$^7$ .......................... C12Q 1/68; C12N 15/80; C07H 21/04; C07K 14/37
(52) U.S. Cl. .......................... 435/6; 435/7.1; 435/455; 435/252.3; 435/69.1; 435/183; 435/471; 435/484; 435/254.11; 435/320.1; 536/23.1; 536/23.2; 536/23.7; 536/24.1; 530/350; 530/371
(58) Field of Search ......................... 435/6, 7.1, 455, 435/252.3, 69.1, 183, 471, 484, 254.11, 320.1; 536/23.1, 23.2, 23.7, 24.1, 23.74; 530/350, 371

(56) References Cited

U.S. PATENT DOCUMENTS

| 4,387,162 A | 6/1983 | Aigle et al. ............ 435/254.21 |
| 5,821,090 A | 10/1998 | Revuelta Doval et al. .... 435/88 |

FOREIGN PATENT DOCUMENTS

| CA | 2223877 | 1/1997 |
| DE | 44 20 785 | 10/1995 |
| EP | 011 562 | 5/1980 |
| WO | WO92/00379 | 1/1992 |
| WO | WO97/03208 | 1/1997 |

OTHER PUBLICATIONS

Merck Index, p. 1183–1184, 1983.
Yeast, vol. 12,No. 9,Jul.1996, Cost et al., pp. 939–941.
Appl.andEnv.Micro, Dec. 1994,4245–4254, Yang et al., vol. 60, No. 12.
Nucl.Acids,Res.,vol. 18,No. 23, Dec. 11, 1990,Berges et al., pp. 7183.
Yeast vol. 9,No.1, Jan. 1993,Bergkamp et al., pp. 677–681.
Yeast vol. 10,No. 10,Oct. 1994, Piredda et al., pp. 1601–1612.
Current Genetics, vol. 23,19/93,Ohkuma et al., 1993, pp. 205–210.
Nucleic Acids Res.,vol. 16,No. 5,1988,p. 2339,Wilson et al.
Current Genetics,vol. 16,1989,Jacobs et al. 159–163.
J.Fermentation and Bio.,vol. 73,No. 1 1992, pp. 255–260, Sakai et al.
Gene,61(1987)385–399,Oakley et al.
Gene,116(1992)59–67, Benito et al.
Mol.Gen Genet (1990) 224:269–278, Minguez et al.
Nuc.Acids Res.,vol. 16, No. 16, 1998, p. 8177, Cantoral et al.
CurrGenet (1995) 27:536–540, Gouka et al.
Gene,29(1984)113–124, Rose et al.
MolGenGenet (1984) 197:345–346; Boeke et al.
Genetics,vol. 140, Jul. 1995, No. 3,Steiner et al.,973–987.
Yeast,vol. 2,163–167(1986), Hill et al.
Genetics,vol. 122,May, 1989,No. 1, Sikorski et al.,19–27.
Mol.andCel Bio.,Oct. 1989, 4432–4449, vol. 9, No. 10, Kramer.
J.Mol.Biol.(1990)215–410,Altschul et al.
Gene,109(1991)99–105,Wright et al.
Gene,142 (1994)135–140,Zhou et al.
Curr Genet(1996) 30:76–82, d'Enfert.
MGG,vol. 248, No. 1, Jul. 22, 1995, A22218.
Mol.GenGenet(1995)248:126–135, Benito et al.

*Primary Examiner*—David Guzo
(74) *Attorney, Agent, or Firm*—Novak Druce DeLuca & Quigg

(57) ABSTRACT

The invention relates to an orotidine-5'-phosphate decarboxylase gene having the sequence of SEQ ID NO: 1 or its homologs, to a gene construct comprising this gene or its homologs, and to its use. The invention additionally relates to vectors or organisms comprising an orotidine-5'-phosphate decarboxylases gene having the sequence SEQ ID NO: 1 or its homologs. The invention further relates to a process for producing uracil-auxotrophic microorganisms and to a process for inserting DNA into uracil-auxotrophic microorganisms.

15 Claims, 1 Drawing Sheet

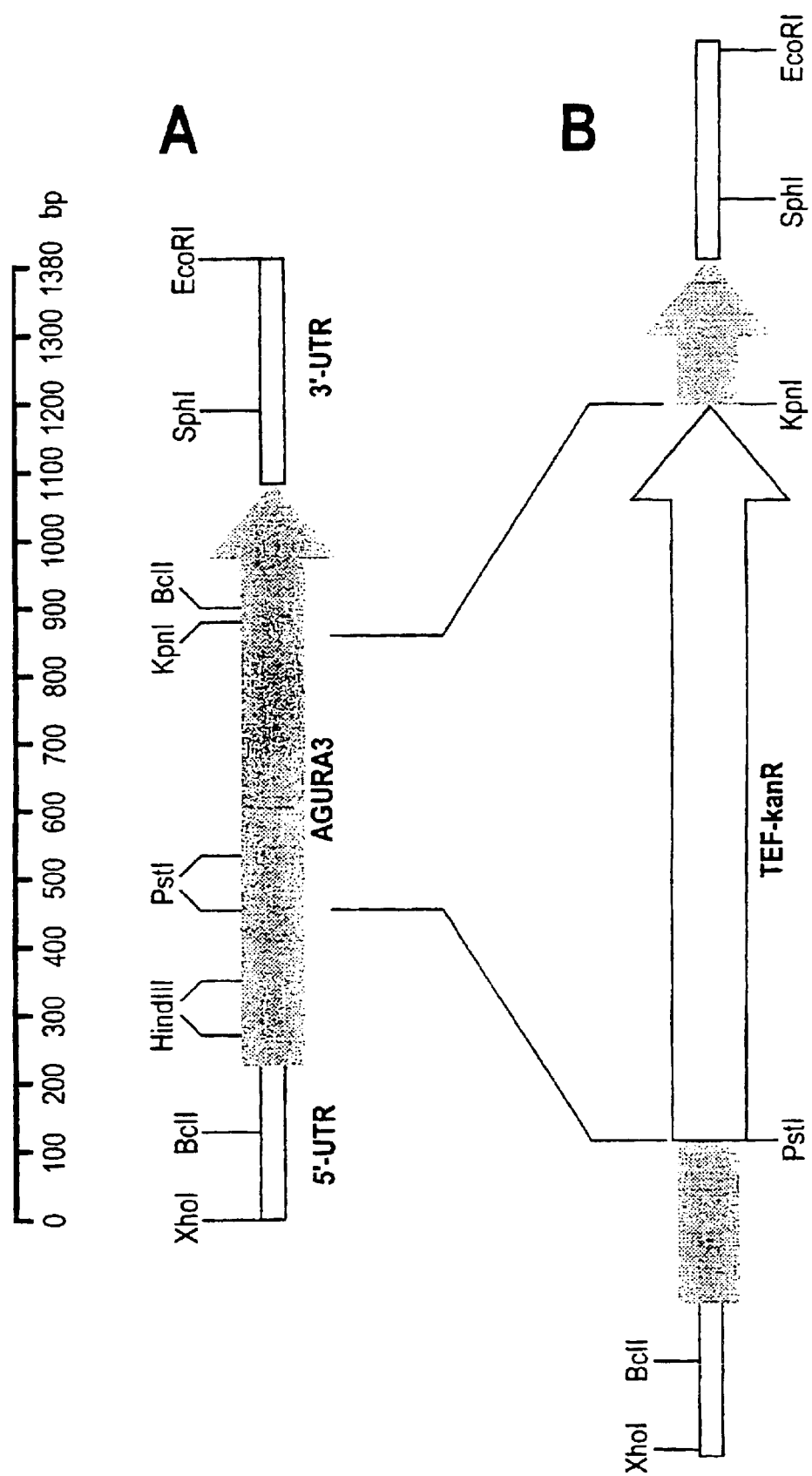

SEQUENCE LISTING

```
<160> NUMBER OF SEQ ID NOS: 6

<210> SEQ ID NO 1
<211> LENGTH: 1380
<212> TYPE: DNA
<213> ORGANISM: Ashbya gossypii
<220> FEATURE:
<221> NAME/KEY: CDS
<222> LOCATION: 210 ... 1013

<400> SEQUENCE: 1
ctcgagcaac tcattggaag cccttcgcaa acgacctcta tatctcgtct caagttccta     60
ctatcatgta tgctgtcact acagaaaaat ttttgtctat agctggcaag aagcacatca    120
catacattct gatggtgtag gctccacatc acagtaagca tttgtataag gctgatcaca    180
```

-continued

| | |
|---|---|
| tagggtgcta ccgacctagc cattgccac atg tca acg aaa tct tac gca gaa<br>                                                  Met Ser Thr Lys Ser Tyr Ala Glu<br>                                                      1             5 | 233 |
| agg gcc aag gca cac aat tcg cca gtt gct aga aag ctt ctg gca ttg<br>Arg Ala Lys Ala His Asn Ser Pro Val Ala Arg Lys Leu Leu Ala Leu<br>          10                       15                       20 | 281 |
| atg cac gag aag aaa acc aat ctc tgc gct tcc ctt gat gtg cgg acg<br>Met His Glu Lys Lys Thr Asn Leu Cys Ala Ser Leu Asp Val Arg Thr<br>25                   30                       35                       40 | 329 |
| tct aga aag ctt ctg gag cta gca gac acg ctg gga ccg cac att tgt<br>Ser Arg Lys Leu Leu Glu Leu Ala Asp Thr Leu Gly Pro His Ile Cys<br>                   45                       50                       55 | 377 |
| ctg ctg aag aca cat gtc gac ata ctg acg gac ttc gac atc gag acg<br>Leu Leu Lys Thr His Val Asp Ile Leu Thr Asp Phe Asp Ile Glu Thr<br>                  60                       65                       70 | 425 |
| aca gtc aag ccg ctg cag cag ctt gcg gct aag cac aac ttc atg atc<br>Thr Val Lys Pro Leu Gln Gln Leu Ala Ala Lys His Asn Phe Met Ile<br>         75                       80                       85 | 473 |
| ttc gag gac cgc aag ttc gct gac att ggc aac acg gtt aag ctg cag<br>Phe Glu Asp Arg Lys Phe Ala Asp Ile Gly Asn Thr Val Lys Leu Gln<br>90                   95                      100 | 521 |
| tac tcc tcc ggc gtg tac cgt atc gcg gag tgg gcg gat att acc aat<br>Tyr Ser Ser Gly Val Tyr Arg Ile Ala Glu Trp Ala Asp Ile Thr Asn<br>105                 110                 115                 120 | 569 |
| gca cac ggc gtc acc ggc ccc ggt gtg ata gcc ggg ctg aag gag gct<br>Ala His Gly Val Thr Gly Pro Gly Val Ile Ala Gly Leu Lys Glu Ala<br>                        125                 130                 135 | 617 |
| gcg aaa ctg gcc tca cag gaa ccc agg ggg ttg ctg atg ctg gca gag<br>Ala Lys Leu Ala Ser Gln Glu Pro Arg Gly Leu Leu Met Leu Ala Glu<br>                140                     145                 150 | 665 |
| ctc tct tct cag ggc tct ttg gcg cgc gga gac tat acc gcg ggc gtc<br>Leu Ser Ser Gln Gly Ser Leu Ala Arg Gly Asp Tyr Thr Ala Gly Val<br>                    155                 160                 165 | 713 |
| gtt gaa atg gcg aag ctg gac gaa gac ttt gtg atc ggg ttc atc gcg<br>Val Glu Met Ala Lys Leu Asp Glu Asp Phe Val Ile Gly Phe Ile Ala<br>170                 175                 180 | 761 |
| cag cgt gac atg ggt ggg cgt gca gac ggc ttt gac tgg ctc atc atg<br>Gln Arg Asp Met Gly Gly Arg Ala Asp Gly Phe Asp Trp Leu Ile Met<br>185               190                 195               200 | 809 |
| acc ccg ggg gtt ggc ctg gac gac aaa gga gac ggc ctg ggc cag cag<br>Thr Pro Gly Val Gly Leu Asp Asp Lys Gly Asp Gly Leu Gly Gln Gln<br>                    205                 210                 215 | 857 |
| tac cgc acg gtg gat gag gtc gtc agc gac ggt acc gat gtg atc att<br>Tyr Arg Thr Val Asp Glu Val Val Ser Asp Gly Thr Asp Val Ile Ile<br>                220                     225                 230 | 905 |
| gtt ggc aga ggg ctc ttt gac aag gga aga gac ccc aag gtc gag ggt<br>Val Gly Arg Gly Leu Phe Asp Lys Gly Arg Asp Pro Lys Val Glu Gly<br>                    235                 240                 245 | 953 |
| gcc cgc tac cgc aag gcc ggt tgg gag gct tac ttg cgc cgt atg ggc<br>Ala Arg Tyr Arg Lys Ala Gly Trp Glu Ala Tyr Leu Arg Arg Met Gly<br>             250                     255                 260 | 1001 |
| gag act tcg tagtctatcg ctggcgccca cagtatatag gcggattcca<br>Glu Thr Ser<br>265 | 1050 |
| ccgccgatta ccatctcagc aaccttttg taattatatg cccctattgc ccttatttcc | 1110 |
| gagctggtgc cgggatcggt ttatagacgg gcaacaagtt gatactttgt tcagtagcat | 1170 |
| gcatccaaca cttgcaggct tggggtgtgg aaggcctcgc cgcggataat tcgtattacc | 1230 |
| cgcacttcgt gaagtattgc tttatgaaaa atcttcactt tgggctaact agagccataa | 1290 |

```
ctcgacacaa gccccttcct acacacttcg agctgggact aaagtgacaa cgaatagcaa    1350
ataattagca aatatggatg cgttgaattc                                     1380
```

<210> SEQ ID NO 2
<211> LENGTH: 267
<212> TYPE: PRT
<213> ORGANISM: Ashbya gossypii

<400> SEQUENCE: 2

```
Met Ser Thr Lys Ser Tyr Ala Glu Arg Ala Lys Ala His Asn Ser Pro
 1               5                  10                  15

Val Ala Arg Lys Leu Leu Ala Leu Met His Glu Lys Lys Thr Asn Leu
                20                  25                  30

Cys Ala Ser Leu Asp Val Arg Thr Ser Arg Lys Leu Leu Glu Leu Ala
            35                  40                  45

Asp Thr Leu Gly Pro His Ile Cys Leu Leu Lys Thr His Val Asp Ile
        50                  55                  60

Leu Thr Asp Phe Asp Ile Glu Thr Thr Val Lys Pro Leu Gln Gln Leu
 65                 70                  75                  80

Ala Ala Lys His Asn Phe Met Ile Phe Glu Asp Arg Lys Phe Ala Asp
                85                  90                  95

Ile Gly Asn Thr Val Lys Leu Gln Tyr Ser Ser Gly Val Tyr Arg Ile
            100                 105                 110

Ala Glu Trp Ala Asp Ile Thr Asn Ala His Gly Val Thr Gly Pro Gly
        115                 120                 125

Val Ile Ala Gly Leu Lys Glu Ala Lys Leu Ala Ser Gln Glu Pro
130                 135                 140

Arg Gly Leu Leu Met Leu Ala Glu Leu Ser Ser Gln Gly Ser Leu Ala
145                 150                 155                 160

Arg Gly Asp Tyr Thr Ala Gly Val Val Glu Met Ala Lys Leu Asp Glu
                165                 170                 175

Asp Phe Val Ile Gly Phe Ile Ala Gln Arg Asp Met Gly Gly Arg Ala
            180                 185                 190

Asp Gly Phe Asp Trp Leu Ile Met Thr Pro Gly Val Gly Leu Asp Asp
        195                 200                 205

Lys Gly Asp Gly Leu Gly Gln Gln Tyr Arg Thr Val Asp Glu Val Val
    210                 215                 220

Ser Asp Gly Thr Asp Val Ile Val Gly Arg Gly Leu Phe Asp Lys
225                 230                 235                 240

Gly Arg Asp Pro Lys Val Glu Gly Ala Arg Tyr Arg Lys Ala Gly Trp
                245                 250                 255

Glu Ala Tyr Leu Arg Arg Met Gly Glu Thr Ser
            260                 265
```

<210> SEQ ID NO 3
<211> LENGTH: 18
<212> TYPE: DNA
<213> ORGANISM: Unknown
<220> FEATURE:
<221> NAME/KEY: misc_feature
<222> LOCATION: 1 ... 18
<223> OTHER INFORMATION: n represents g, a, t or c
<223> OTHER INFORMATION: oligonucleotide as primer for PCR

<400> SEQUENCE: 3

```
ytnggnccnt ayathtgy                                                     18
```

```
<210> SEQ ID NO 4
<211> LENGTH: 23
<212> TYPE: DNA
<213> ORGANISM: Unknown
<220> FEATURE:
<221> NAME/KEY: misc_feature
<222> LOCATION: 1 ... 23
<223> OTHER INFORMATION: n represents g, a, t or c
<223> OTHER INFORMATION: oligonucleotide as primer for PCR

<400> SEQUENCE: 4
taytgytgnc cnaryttrtc ncc                                        23

<210> SEQ ID NO 5
<211> LENGTH: 26
<212> TYPE: DNA
<213> ORGANISM: Unknown
<220> FEATURE:
<221> NAME/KEY: misc_feature
<222> LOCATION: 1 ... 26
<223> OTHER INFORMATION: n represents g, a, t or c
<223> OTHER INFORMATION: oligonucleotide as primer for PCR

<400> SEQUENCE: 5
ttyytnatht tygargaymg naartt                                     26

<210> SEQ ID NO 6
<211> LENGTH: 19
<212> TYPE: DNA
<213> ORGANISM: Unknown
<220> FEATURE:
<221> NAME/KEY: misc_feature
<222> LOCATION: 1 ... 19
<223> OTHER INFORMATION: n represents g, a, t or c
<223> OTHER INFORMATION: oligonucleotide as primer for PCR

<400> SEQUENCE: 6
gcnarnarna rnarnccnc                                             19
```

OROTIDINE-5'-PHOSPHATE DECARBOXYLASE-GENE, GENE CONSTRUCT CONTAINING SAID GENE AND THE UTILIZATION THEREOF

The invention relates to an orotidine-5'-phosphate decarboxylase gene having the sequence SEQ ID No. 1 or its homologs, to a gene construct comprising this gene or its homologs, and to its use.

The invention additionally relates to vectors or organisms comprising an orotidine-5'-phosphate decarboxylase gene having the sequence SEQ ID No. 1 or its homologs.

The invention further relates to a process for producing uracil-auxotrophic microorganisms and to a process for inserting DNA into uracil-auxotrophic microorganisms.

Vitamin B2, also called riboflavin, is essential for humans and animals. Vitamin B2 deficiency is associated with inflammations of the mucosa of the mouth and throat, pruritus and inflammations in skin folds and similar cutaneous lesions, conjunctival inflammations, reduced visual acuity and clouding of the cornea. In babies and children, cessation of growth and weight loss may occur. Vitamin B2 therefore has economic importance in particular as vitamin supplement in cases of vitamin deficiency and as animal feed supplement. It is additionally used as food color, for example in mayonnaise, ice cream, blancmange etc.

Vitamin B2 is prepared either chemically or microbially (see, for example, Kurth et al., 1996, Riboflavin, in: Ullmann's Encyclopedia of industrial chemistry, VCH Weinheim). In the chemical preparation processes, riboflavin is usually obtained as pure final product in multistage processes, it being necessary to employ relatively costly starting materials such as, for example, D-ribose. An alternative to the chemical synthesis of riboflavin is the preparation of this substance by microorganisms. The starting materials used in this case are renewable raw materials such as sugars or vegetable oils. The preparation of riboflavin by fermentation of fungi such as *Eremothecium ashbyii* or *Ashbya gossypii* is known (The Merck Index, Windholz et al., eds. Merck & Co., page 1183, 1983), but yeasts such as, for example, *Candida, Pichia* and *Saccharomyces* or bacteria such as, for example, *Bacillus*, clostridia or *corynebacteria* have also been described as riboflavin producers.

DE 44 20 785 describes six riboflavin biosynthesis genes from *Ashbya gossypii*, and microorganisms which have been transformed with these genes, and the use of such microorganisms for riboflavin synthesis.

To date, genes have been inserted into fungal riboflavin producers such as *Ashbya gossypii* via the markers leu2 (leucine auxotrophy), thr4 (threonine auxotrophy) or kan (kanamycin resistance) (WO 92/00379). A further marker described in yeasts is met15 (methionine auxotrophy, Cost et al., Yeast, Vol. 12, 1996: 939–941). The disadvantage of this marker is that either the transformation efficiency is very low and/or antibiotics must be continuously added for the selection. However, in each case, counterselection for loss of the marker with retention of the inserted genes in microorganisms is impossible or possible only with very great effort, so that it is usually no longer possible to insert further genes with these markers into the microorganisms. It is therefore desirable to have a selection marker which displays high transformation efficiency, is easily selectable and makes counterselection possible.

The orotidine-5'-phosphate decarboxylase gene (=URA3 gene) from *Saccharomyces cerevisiae* is one of the classical markers having the required properties and usable for transforming genes into microorganisms such as yeasts and fungi.

The isolation of species-specific URA3 genes and the isolation of the corresponding gene from fungi (=pyrG) and the sequences thereof from *Pichia stipitis, Candida boidinii, Kluyveromyces marxianus, Yamadazyma ohmeri, Candida maltosa, Aspergillus niger, Aspergillus oryzae, Aspergillus nidulans, mucor circinelloides, Phycomyces blakesleeanus, Penicillium chrysogenum*, and *Aspergillus awamori* have been described in a number of studies (Appl. Environ. Microbiol., Vol. 60, No. 12, 1994:4245–4254, Nucl. Acids Res., Vol. 18, No. 23, 1990: 7183, J. Ferment. Bioeng., Vol. 73, No 4, 1992: 255–260, Yeast, Vol. 9, 1993: 677–681, Yeast, Vol. 10, 1994: 1601–1612, Curr. Genet., Vol. 23, 1993: 205–210, Nucl. Acids Res., Vol. 16, No. 5, 1988: 2339, Curr. Genet., Vol. 16, 1989: 159–163, Gene, Vol. 61, 1987: 385–399, Gene, Vol. 116, 1992: 59–67, Mol. Gen. Genet., Vol. 224, 1990: 269–278, Nucl. Acids Res., Vol. 16, No. 16, 1988: 8177, Nucl. Acids Res., Vol. 18, No. 23, 1990: 7183 and Curr. Genet., Vol. 27, 1995: 536–540).

Studies by Rose et al. (Gene, Vol. 29, 1984: 113–124) have shown that the URA3 gene from *Saccharomyces cerevisiae* is in fact capable of complementation of a corresponding mutation (pyrF gene=URA3) in prokaryotes such as *Escherichia coli*, and can be useful as selection marker.

However, genetic studies on riboflavin synthesis by *Ashbya gossypii* (vitamin B2 synthesis) have shown that the URA3 gene from *Saccharomyces cerevisiae* or the pyrF gene from *Escherichia coli* are not capable of complementation of uracil-auxotrophic *Ashbya gossypii* mutants, and therefore these genes cannot be used for cloning genes into *Ashbya gossypii*.

Attempts have therefore been made, because that gene from 5 *Ashbya gossypii* corresponding to the URA3 gene or pyrF gene is unknown, to clone it. Attempts at cloning the *Ashbya* gene by the methods described in the literature via, for example, hybridization with URA3 gene fragments or via degenerate oligonucleotides based on conserved amino-acid sequences of various orotidine-5'-phosphate decarboxylases and screening a cDNA library using these oligonucleotides and the PCR technique were unsuccessful (Bergkamp et al. Yeast, Vol. 9,1993: 677–681, Piredda et al., Yeast, Vol 0.10, 1994: 1601–1612, Benito et al., Gene, Vol. 116, 1992: 59–67 and Diaz-Minguez et al. Mol. Gen. Genet. Vol. 224.1990: 269–278).

It is an object of the present invention therefore to provide an easily selectable marker which can be transformed with high yield and is easily counterselectable and which makes it possible to insert genes into microorganisms.

We have found that this object is achieved by the novel orotidine-5'-phosphate decarboxylase gene having the sequence SEQ ID NO: 1 or its homologs which have at least 80% homology with the sequence SEQ ID NO: 1.

BRIEF DESCRIPTION OF DRAWINGS

FIG. 1 is a pictorial depiction of the XhoI-SphI fragment of the construct ura 3::G418.

Homologs of the novel orotidine-5'-phosphate decarboxylase gene having the sequence SEQ ID NO: 1 mean, for example, allelic variants which have at least 80% homology at the derived amino-acid level, preferably at least 90% homology, very particularly preferably at least 95% homology. The amino-acid sequence derived from SEQ ID NO: 1 is to be seen in SEQ ID NO: 2. Allelic variants comprise, in particular, functional variants which are obtainable by deletion, insertion or substitution of nucleotides from the sequence depicted in SEQ ID NO: 1, the intention being, however, that the enzymatic activity of the derived synthesized proteins advantageously be retained for the insertion of one or more genes. However, if the intention is to produce mutants in the orotidine-5'-phosphate decarboxylase gene with the aid of SEQ ID NO: 1 and its homologs in the novel process for producing uracil-auxotrophic microorganisms, non-functional genes will be used, that is to say genes which lead to enzymatically inactive proteins. In this case, it is advantageous to use sequences which display homologs with SEQ ID NO: 1 or its homologs advantageously at the 3' and 5' ends.

Homologs of SEQ ID NO: 1 additionally mean, for example, fungal or plant homologs, truncated sequences, single-stranded DNA or RNA of the coding and noncoding DNA sequence. Homologs of SEQ ID NO: 1 have at the DNA level a homology of at least 60%, preferably of at least 70%, particularly preferably of at least 80%, very particularly preferably of at least 90%, over the complete DNA region indicated in SEQ ID NO: 1.

Homologs of SEQ ID NO: 1 also mean derivatives such as, for example, promoter variants. The promoters upstream of the indicated nucleotide sequences may be modified by one or more nucleotide exchanges, by insertion(s) and/or deletion(s) without, however, the functionality or activity of the promoters being impaired. It is additionally possible for the promoters to have their activity increased by modifying their sequence, or to be completely replaced by more active promoters even from heterologous organisms.

Derivatives also mean variants whose nucleotide sequence in the region from −1 to −200 in front of the start codon have been modified so as to alter, preferably increase, gene expression and/or protein expression.

It is possible and preferred for SEQ ID NO: 1 or its homologs to be isolated from microorganisms of the family Metschnikowiaceae, particularly preferably from microorganisms of the genera Eremothecium, *Ashbya* or Nematospora, very particularly preferably from microorganisms of the genus and species Eremothecium ashbyii or *Ashbya gossypii*.

The novel gene construct means the URA3 gene sequences SEQ ID No. 1 and its homologs which have been functionally linked to one or more regulatory signals, advantageously to increase gene expression. Examples of these regulatory sequences are sequences to which inducers or repressors bind and thus regulate the expression of the nucleic acid. In addition to these novel regulatory sequences, the natural regulation of these sequences in front of the actual structural genes can still be present and, where appropriate, have been genetically modified so that the natural regulation has been switched off and the expression of the genes has been increased. The gene construct can, however, also have a simpler structure, that is to say no additional regulatory signals have been inserted in front of the sequence SEQ ID No. 1 or its homologs, and the natural promoter with its regulation has not been deleted. Instead, the natural regulatory sequence has been mutated so that regulation no longer takes place, and gene expression is enhanced. The gene construct may additionally advantageously comprise one or more so-called enhancer sequences functionally linked to the promoter and making increased expression of the nucleic acid sequence possible. It is also possible to insert at the 3' end of the DNA sequences additional advantageous sequences, such as further regulatory elements or terminators. The URA3 genes may be present in one or more copies in the gene construct, and the gene or genes can also be inactivated. It is possible with the aid of this or these inactivated genes to generate uracil-auxotrophic mutants in the novel process. It is advantageous for further genes to be present in the gene construct for insertion of further genes into a microorganism. These genes may be located inside a URA3 gene, in which case there ought advantageously to be an intact copy of the URA3 gene and/or another selectable gene such as leu2, thr4 or kan present in the construct, or they can be located outside the URA3 gene. Even if an intact URA3 gene is present in the construct, further markers such as those mentioned above can, where appropriate, be present for selection in the gene construct.

Advantageous regulatory sequences for the novel process are present, for example, in promoters such as cos, tac, trp, tet, trp-tet, lpp, lac, lpp-lac, lacIq, T7, T5, T3, gal, trc, ara, SP6, $\lambda$-$P_R$ or $\lambda$-$P_L$ promoter and are advantageously used in Gram-negative bacteria. Further advantageous regulatory sequences are present, for example, in the Gram-positive promoters amy and SPO2, in the yeast or fungal promoters ADC1, MF$\alpha$, AC, P-60, CYC1, GAPDH, TEF, rp28, ADH or in the plant promoters CaMV/35S, SSU, OCS, lib4, usp, STLS1, B33, nos or in the ubiquitin or phaseolin promoter. Also advantageous in this connection are the promoters of pyruvate decarboxylase and of methanol oxidase from, for example, *Hansenula*. It is also possible to use artificial promoters for the regulation.

It is possible in principle to use all natural promoters with their regulatory sequences like those mentioned above for the novel process. It is also possible and advantageous in addition to use synthetic promoters.

The gene construct may, as described above, also comprise further genes which are to be inserted into the microorganisms. These genes can be inserted inside or outside the marker genes such as ura3, leu2, thr4 or kan. It is possible in principle for all types of genes to be inserted into microorganisms with the aid of the novel URA3 gene having the sequence SEQ ID NO: 1 or its homologs. It is possible and advantageous to insert and express in host organisms regulatory genes such as genes for inducers, repressors or enzymes which intervene by their enzymatic activity in the regulation, or one or more or all genes of a biosynthetic pathway such as the genes of riboflavin biosynthesis such as, for example, the rib genes or genes of biosynthetic pathways which lead to other fine chemicals, secondary metabolites or proteins, such as the genes of biotin, lysine, methionine, vitamin B12 or carotenoid biosynthesis, or genes which lead to flavorings, growth promoters or odoriferous substances, or individual genes for enzymes such as proteases or lipases, via the URA3 sequence. These genes can be heterologous or homologous in origin. The inserted genes may have their own promoter or else be under the control of the promoter of the sequence SEQ ID No. 1 or its homologs.

For expression in the abovementioned host organism, the gene construct is advantageously inserted into a vector such as, for example, a plasmid, a phage or other DNA, which makes optimal expression of the genes in the host possible. Examples of suitable plasmids are, in *E. coli*, pLG338, pACYC184, pBR322, pUc18, pUC19, pKC30, pRep4, pHS1, pHS2, pPLc236, pMBL24, pLG200, pUR290, pIN-III[113]-B1, kgt11 or pBdCI, in *Streptomyces*, pIJ101, pIJ364, pIJ702 or pIJ361, in *Bacillus*, pUB110, pC194 or pBD214, in *Corynebacterium*, pSA77 or pAJ667, in fungi, pALS1, pIL2 or pBB116, in yeasts, 2$\mu$m, pAG-1, YEp6, YEp13 or pEMBLYe23, or, in plants, pLGV23, pGHlac$^+$, pBIN19, pAK2004 or pDH51. Said plasmids represent a small selection from the possible plasmids. Further plasmids are well known to the skilled worker and can be found, for example, in the book Cloning Vectors (Eds. Pouwels P. H. et al. Elsevier, Amsterdam-New York-Oxford, 1985, ISBN 0 444 904018).

The gene construct advantageously comprises, for expression of the other genes present, additionally 3' and/or 5' terminal regulatory sequences to enhance expression, which are selected for optimal expression depending on the selected host organism and gene or genes.

These regulatory sequences are intended to make specific expression of the genes and protein expression possible. This may mean, depending on the host organism, for example that the gene is expressed or overexpressed only after induction, or that it is immediately expressed and/or overexpressed.

The regulatory sequences or factors may moreover preferably have a beneficial effect on expression of the introduced genes, and thus increase it. It is possible in this way for the regulatory elements to be enhanced advantageously at the transcription level by using strong transcription signals such as promoters and/or enhancers. However, in addition, it is also possible to enhance translation by, for example, improving the stability of the mRNA.

In a further embodiment of the vector, the novel gene construct can also be advantageously introduced in the form of a linear DNA into the microorganisms and be integrated into the genome of the host organism by heterologous or homologous recombination. This linear DNA can consist of a linearized plasmid or only of the gene construct as vector.

Host organisms suitable in principle for the novel gene construct are all prokaryotic or eukaryotic organisms. The host organisms advantageously used are microorganisms such as bacteria, fungi, yeasts, animal or plant cells. Fungi or yeasts are preferably used, particularly preferably fungi, very particularly preferably fungi of the family Metschnikowiaceae such as Eremothecium, *Ashbya* or Nematospora.

The invention additionally relates to a process for producing uracil-auxotrophic microorganisms. To generate uracil-auxotrophic mutants, the orotidine-5'-phosphate decarboxylase gene having SEQ ID NO: 1 or its homologs are modified, for example by mutagenesis, in such a way that the protein encoded by the gene is inactivated. This inactivated gene is subsequently introduced into a microorganism, for example by transformation or electroporation. Finally, homologous recombination in the microorganisms results in auxotrophic mutants which can be screened via their resistance to 5-fluoroorotic acid (see Boeke et al., Mol. Gen. Genet., Vol. 197, 1984: 345–346).

The invention further relates to a process for inserting DNA into organisms, which comprises inserting into an organism, preferably a microorganism, which is deficient in an orotidine-5'-phosphate decarboxylase gene (=URA3 gene) a vector which comprises an intact URA3 gene having the sequence SEQ ID NO:1 or its homologs, advantageously together with further DNA, preferably with at least one other gene, and cultivating this organism on or in a culture medium which contains no uracil. Only these organisms which have acquired the vector are able to grow in this medium. A linear DNA is preferably used as vector in this process. The microorganisms preferably used in this process are fungi, especially of the family Metschnikowiaceae such as *Eremothecium, Ashbya* or *Nematosprora*, particularly preferably microorganisms of the genus *Ashbya*.

It is also possible to use as vector any suitable plasmid (but especially a plasmid which harbors the origin of replication of the 2 m plasmid from *S. cerevisiae*) which undergoes autonomous replication in the cell, but also, as described above, a linear DNA fragment which is integrated into the genome of the host. This integration can take place by heterologous or homologous recombination. But preferably, as mentioned, by homologous recombination (Steiner et al., Genetics, Vol. 140, 1995: 973–987).

The novel URA3 gene having the sequence SEQ ID NO: 1 or its homologs can advantageously be used as selection markers in the novel process. It is possible and preferred to insert genes using these selection marker genes into *Ashbya gossypii*.

An additional advantage is that on transformation of *Ashbya gossypii* it is possible to select with the aid of this gene, without the need to use foreign DNA (i.e. DNA not derived from *Ashbya gossypii*).

It is possible on transformation of *Ashbya gossypii* with the gene having SEQ ID NO: 1 or its homologs also to insert any other genes. This makes it possible to construct strains which harbor single genes or a plurality of genes in several copies either on plasmids or in the genome.

It is further possible to construct *Ashbya* strains in which chromosomal copies of genes have been destroyed by the insertion of the URA3 gene having SEQ ID NO: 1 or its homologs.

A particular advantage of the AgURA3 gene is the possibility of using the marker several times in succession in the same strain.

If identical nucleotide sequences are placed 5' and 3' of the gene in the same orientation (so-called direct repeats), it is possible if required to delete the AgURA3 marker again by homologous recombination and selection on uracil- and FOA-containing medium, and then in another round insert additional DNA with the aid of this gene. Another advantage is the distinctly greater transformation efficiency by comparison with the markers thr, leu or kan.

In the novel process, the vector comprises as other gene at least one gene of riboflavin synthesis. Genes of riboflavin synthesis mean those genes which are involved in synthesis in the entire metabolism of riboflavin producers such as *Ashbya*.

EXAMPLES

Example 1

Production of a Genomic Gene Bank from *Ashbya gossypii* ATCC10895

Genomic DNA from *Ashbya gossypii* ATCC 10895 was prepared by the process described in WO97/03208. The genomic gene bank derived from this DNA was constructed in pRS314 and in YEp351 (Hill et al., Yeast, Vol. 2, 1986: 163–167) by the method described in Sambrook, J. et al. (1989) Molecular cloning: A laboratory manual, Cold Spring Harbor Laboratory Press or in F. M. et al. (1994) Current protocol in molecular biology, John Wiley and Sons. As can be inferred from, for example, WO97/03208, other plasmids, such as plasmids of the pRS series (Sikorski and Hieter, Genetics, 1989: 19–27) or cosmids such, as, for example, SuperCos1 (Stratagene, La Jolla, USA), are also suitable for producing the gene bank.

Example 2

It was initially attempted to clone the gene for the orotidine-5'-phosphate decarboxylase (=OMP-DC) from *Ashbya gossypii* via functional complementation of a corresponding URA3-auxotrophic mutant of *Saccharomyces cerevisiae*.

To this end, a gene bank was constructed from genomic *Ashbya gossypii* DNA in pRS314 (as described in Example 1). This DNA was used to transform the *S. cerevisiae* strain MW3317-21A (genotype: MAT α, trp1, ade8ΔKpn, ura3–52, hom3–10, metl3, met4, ade2, his3-Kpn, see, for example, Kramer et al., Mol. Cell. Biol. 9, 1989: 4432–4440), by the lithium acetate method (see, for example, Kramer et al., Mol. Cell. Biol. 9, 1989: 4432–4440). No clone in which the genomic deletion of the ura3 gene of the *S. cerevisiae* strain was complemented by a gene fragment from *Ashbya* was obtained.

The attempt to clone the URA3 gene of *Ashbya gossypii* via functional complementation in a pyrF mutant of *E. coli* also failed.

Example 3

An attempt to clone the OMP-DC gene from *Ashbya gossypii* by hybridization with a fragment of the corresponding gene from 45 *Saccharomyces cerevisiae* was also unsuccessful.

For this purpose, the complete URA3 gene from *Saccharomyces cerevisiae* (gene bank entry yscodcd) was used as probe (length 1.1 kb) in order to screen a genomic cosmid gene bank from *Ashbya gossypii* (se e Example 1). The experiment was carried out as described in Sambrook, J. et al. (1989) molecular cloning: A laboratory manual, Cold Spring Harbor Laboratory Press or Ausubel, F. M. et al. (1994) Current protocols in molecular biology, John Wiley and Sons, using hybridization temperatures of 52° C. to 68° C. It was not possible to identify in the gene bank any clones which provided a positive signal with the URA3 gene from *S. cerevisiae* as probe.

Example 4

In the next approach, it was attempted to clone the gene for OMP-DC from *Ashbya gossypii* by amplification of gene fragments using degenerate oligonucleotides and the PCR technique.

For this experiment, the known amino-acid sequences of the various orotidine-5'-phosphate decarboxylases from the following organisms were compared, and regions showing maximum conservation in all the enzymes were selected:

*Aspergillus niger* (Acc. number: P07817)

*Aspergillus nidulans* (Acc. number: P10652)

*Schizosaccharomyces pombe* (Acc. number: P14965)

*Penicillium chrysogenum* (ACC. number: P09463)

*Kluyveromyces lactis* (Acc. number: P07922)

*Candida albicans* (Acc. number: P13649)

*Neurospora crassa* (Acc. number: P05035)

*Ustilago* maydis (Acc. number: P15188)

*Saccharomyces cerevisiae* (Acc. number: $PO_{3962}$)

*Drosophila melanogaster* (Acc. number: Q01637)

Mouse (Acc. number: P13439)

Human (Acc. number: P11172)

The numbers given in parentheses are derived from the SWISS&PIR-Translated Datenbank Release 103.

Degenerate olgonucleotides were synthesized on the basis of this information.

Degenerate oligonucleotides mean oligonucleotides in which mixtures of nucleotides have been incorporated at several positions during the synthesis.

In this connection, R represents G or A, Y represents C or T, W represents A or T, M represents A or C, K represents G or T, S represents C or G, H represents A, C or T, V represents A, C or G, B represents C, G or T, D represents A, G or T, and N represents G,A,T or C.

The following oligonucleotides were used:

(SEQ ID NO:3)

URA3-A: 5'-YTNGGNCCNTAYATHTGY-3'

(SEQ ID NO:4)

URA3-B 45'-TAYTGYTGNCCNARYTTRTCNCC-3<<

(SEQ ID NO:5)

URA3-C: 5'-TTYYTNATHTTYGARGAYMGNAARTT-3'

(SEQ ID NO:6)

URA3-D: 5'-GCNARNARNARNARNCCNC-3'

Using these oligonucleotides as primers, PCRs were carried out with genomic DNA from *Ashbya gossypii* as template.

The following primer combinations were used:

URA3-A+URA3-B; URA3-A+URA3-D; URA3C+URA3-B and URA3-C+URA3-D.

The following hybridization temperatures were used:

52° C., 48° C., 44° C., 40° C. and 37° C.

The products resulting from the PCRs were cloned by conventional methods into the vector pGEMT (Promega) and were sequenced. It was not possible to amplify any fragments which showed homology with the known OMP-DC genes mentioned above.

Example 5

A cDNA bank was constructed from *Ashbya gossypii* as described in DE 44 20 785 A1 (Example 1).

Example 6

Analysis of Nucleic Acid Sequences in the Gene Bank

Single clones were selected from *E. coli* clones which comprised the gene bank from *Ashbya gossypii* described in Example 5. The cells were cultivated by conventional methods in suitable media (e.g. Luria broth with 100 mg/l ampicillin), and plasmid DNA was isolated from these cells.

Oligonucleotides which hybridize in the vector portion were used as primers for sequencing the cDNA clones. Fragments of the cloned cDNAs were detected in this way. The sequences were analyzed as described in Example 7.

Example 7

A computer-assisted analysis of the nucleotide sequences found was carried out by comparisons of newly identified sequences with existing DNA and protein data banks using the following algorithms, e.g. with BLAST algorithms (Altschul et al. (1990) J. Mol. Biol. 215, 403–410), the Clustal algorithm with the aid of the PAM250 weighting table or the Wilbur-Lipman DNA alignment algorithm (as implemented, for example, in the program package MegAlign 3.06 supplied by DNAstar). It was possible in this way to discover similarities of the newly discovered sequences with previously known sequences, and to describe the function of novel genes or part-sequences of genes.

Example 8

Identification of *E. coli* Clones which Harbor the Gene for OMP-DC from *Ashbya gossypii* (AgURA3).

After examination of a large number of clones as described in Examples 6 and 7 (>100 clones), a sequence which showed similarities with known OMP-DC genes was found. This homologous process was then used to screen the genomic *Ashbya* gene bank (see Example 1) once again, and it was possible to identify clones and cosmids which gave a specific positive signal and harbored a common 1.3 kb XhoI-EcoRI fragment. Sequencing of the clones produced the sequence as described in SEQ ID NO: 1. The sequence shows similarities with known URA3 genes and codes for a protein about 29246 Dalton in size.

Example 9
Disruption of the Chromosomal Copy of the AgURA3 Gene with Antibiotic Resistance Genes Disruption of a gene means destruction of the functionality of a genomic copy of the gene either by (a) deleting part of the gene sequence or by (b) of the interrupting the gene by introducing a piece of foreign DNA into the gene or by (c) replacing part of the gene by foreign DNA. Any foreign DNA can be used, but it is preferably a gene which effects resistance to any suitable chemical. Any suitable resistance genes can be used to disrupt genes.

To disrupt the AgURA3 gene of *Ashbya gossypii* ATCC10895, the kananycin resistance gene from Tn903, which is under the control of the TEF promoter of *Ashbya gossypii* (see Yeast 10, pages 1793–1808, 1994 or WO92/00379), was used. The gene is flanked 5' and 3' by several cleavage sites for restriction endonucleases, so that it was possible to construct a cassette which makes possible any desired constructions of gene disruptions using conventional methods of in vitro DNA manipulation.

The internal 370 bp PstI-KpnI fragment of AgURA3 (position 442–892 in sequence SEQ ID NO: 1) was replaced by a resistance cassette as outline above. The resulting construct was given the name ura3::G418. The resulting plasmid can be replicated after transformation into *E. coli*. The XhoI-SphI fragment of the construct ura3::G418 (see FIG. 1) was purified by agarose gel electrophoresis and subsequent elution of the DNA from the gel (see Proc. Natl. Acad. Sci. USA 7j, 615–619, 1979) and employed to transform *Ashbya gossypii*. FIG. 1 shows in depiction A a restriction map of the coding region of the AgURA3 gene and of the 5'- and 3'-untranslated regions (=5'-UTR and 3'-UTR). Depiction B shows the situation after insertion of the kanamycin resistance cassette described above (=TEF-kanR).

The fragment was transformed into *Ashbya gossypii* either by protoplast transformation (Gene 109, 99–105, 1991) or else, preferably, by electroporation (BioRad Gene Pulser, conditions: cuvettes with slit widths of 0.4 mm, 1500V, 25μF, 100Ω). The selection of transformed cells took place on G418-containing solid medium (WO 97/03208).

Resulting G418-resistant clones were examined by conventional methods of PCR and Southern blot analysis (Sambrook, J. et al. (1989) Molecular cloning: A laboratory manual, Cold Spring Harbor Laboratory Press and in F. M. et al. (1994) Current protocols in molecular biology, John Wiley and Sons) to find whether the genomic copy of AgURA3 gene was in fact destroyed. Clones whose AgURA3 gene was destroyed are uracil-auxotrophic resistant to 1 mg/ml 5'-fluoroorotic acid (FOA).

Example 10
Disruption of the Chromosomal Copy of the AgURA3 Gene without Using Antibiotic Resistance Genes A particular advantage of the use of URA3 genes is the possibility of selection both for the presence and for the absence of the gene. It is possible to screen with FOA microorganisms which have a functionally inactivated URA3 gene, and by means of selection for uracil prototrophy to select for a functionally active URA3 gene.

To disrupt the genomic copy of the URA3 gene, for the sake of simplicity an internal fragment (=PstI fragment) of the URA3 gene was deleted from the coding region of the gene having the sequence SEQ ID NO: 1 (position 442 to 520 in sequence SEQ ID NO: 1). Transformation of *Ashbya gossypii* with this deleted ura3 fragment was carried out as described in Example 10. In place of deletion of part-regions of the gene, it is also possible in principle to use all other methods for inactivating the gene, such as mutations via insertions, duplications, reversions, replacement of several nucleotides or point mutations. Point mutations are less preferred because reversion thereof is easy.

The transformants were selected through resistance to FOA. In contrast to wild-type clones, clones which harbor a disruption of the AgURA3 gene are resistant to 1 mg/ml FOA.

Example 11

Use of the AgURA3 Gene for Inserting Further DNA into *A. gossypii*.

The isocitrate lyase gene described in WO 97/03208 was inserted with the aid of the plasmid pAG100, as described in WO 97/03208 (Example 4 and 5), into AgURA3 disruption mutants of *A. gossypii* (see Example 9 and 10), using as selection marker in *A. gossypii* the AgURA3 gene in place of the G418 resistance described.

We claim:

1. An isolated orotidine-5'-phosphate decarboxylase gene having the sequence SEQ ID NO: 1 and homologs of said sequence having at least 90% homology on the derived amino acid level.

2. An isolated amino-acid sequence encoded by a gene or its homologs as claimed in claim 1.

3. A gene construct comprising an orotidine-5'-phosphate decarboxylase gene having the sequence SEQ ID No: 1 or its homologs as claimed in claim 1, where the gene or its homologs is functionally linked to one or more regulatory signals.

4. A process for producing uracil-auxotrophic microorganisms, which comprises modifying an orotidine-5'-phosphate decarboxylase gene having the sequence SEQ ID NO: 1 or its homologs as claimed in claim 1 in such a way that the protein encoded by the gene is inactive, and introducing this modified gene into the microorganisms and integrating said gene by homologous recombination into the genome of the microorganisms, and subsequently selecting these microorganisms for resistance to 5-fluoroorotic acid thereby producing uracil-auxotrophic microorganisms.

5. Isolated homologs having 80% homology with the orotidine-5'-phosphate decarboxylase gene claimed in claim 1.

6. An orotidine-5'-phosphate decarboxylase gene having the sequence SEQ ID NO: 1 which is isolated from *Ashbya gossypii*.

7. Isolated homologs of the orotidine-5'-phosphate decarboxylase gene claimed in claim 6.

8. An isolated amino-acid sequence as claimed in claim 2, which comprises an enzymatically active protein.

9. A gene construct as claimed in claim 3, whose gene expression is increased by the regulatory signals.

10. A vector comprising a gene construct as claimed in claim 3.

11. A microorganism comprising at least one gene construct as claimed in claim 3.

12. A process for inserting DNA into microorganisms, which comprises inserting a vector which comprises an intact orotidine-5'-phosphate decarboxylase gene having the sequence SEQ ID NO: 1 or its homologs isolated from microorganisms which have at least 90% homology with the sequence as depicted in SEQ ID NO: 1 together with at least one other nucleic acid sequence, into a microorganism which is deficient in orotidine-5'-phosphate decarboxylase enzymatic activity and cultivating this microorganism on or in a culture medium without uracil.

13. A process as claimed in claim 12, wherein a linear DNA is used as the vector.

14. A process as claimed in claim 12, wherein an *Ashbya gossypii* strain is used as the microorganism deficient in orotidine-5'-phosphate decarboxylase enzymatic activity.

15. A process as claimed in claim 12, wherein at least one gene of riboflavin synthesis is inserted as an additional gene into the microorganism.

* * * * *